(12) United States Patent
Narasimhan et al.

(10) Patent No.: US 7,494,514 B2
(45) Date of Patent: Feb. 24, 2009

(54) METHOD AND COMPOSITIONS FOR COLORING HAIR

(75) Inventors: Saroja Narasimhan, Matawan, NJ (US); Lou Ann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 11/935,540

(22) Filed: Nov. 6, 2007

(65) Prior Publication Data

US 2008/0060142 A1    Mar. 13, 2008

(51) Int. Cl.
*A61Q 5/10* (2006.01)

(52) U.S. Cl. .................. 8/405; 8/406; 8/410; 8/411; 8/412; 8/421; 8/580; 8/594

(58) Field of Classification Search .............. 8/405, 8/406, 410, 411, 412, 421, 580, 594
See application file for complete search history.

(56) References Cited

U.S. PATENT DOCUMENTS

| | | | |
|---|---|---|---|
| 3,555,584 A | 1/1971 | Kalopsis | |
| 3,930,792 A | 1/1976 | Alperin | |
| 4,010,872 A * | 3/1977 | Lozano et al. | 222/94 |
| 4,678,475 A | 7/1987 | Hoshowski | |
| 4,964,874 A | 10/1990 | Saphakkul | |
| 5,279,618 A | 1/1994 | Prota | |
| 5,441,542 A | 8/1995 | Prota | |
| 5,589,177 A | 12/1996 | Herb | |
| 5,628,799 A | 5/1997 | Wenke | |
| 5,643,341 A | 7/1997 | Hirsch | |
| 5,837,661 A | 11/1998 | Evans | |
| 5,843,193 A | 12/1998 | Hawkins | |
| 5,919,273 A | 7/1999 | Rondeau | |
| 5,932,203 A | 8/1999 | Coffindaffer | |
| 5,961,665 A | 10/1999 | Fishman | |
| 5,993,490 A | 11/1999 | Rondeau | |
| 6,001,135 A | 12/1999 | Rondeau | |
| 6,012,462 A | 1/2000 | Schmittou | |
| 6,015,574 A | 1/2000 | Cannell | 424/450 |
| 6,142,157 A | 11/2000 | de Larforcade | |
| 6,221,389 B1 | 4/2001 | Cannell | 424/450 |
| 6,238,653 B1 | 5/2001 | Narasimhan | |
| 6,315,989 B1 | 11/2001 | Narasimhan | |
| 6,368,360 B2 | 4/2002 | Samain | |
| 6,371,994 B2 | 4/2002 | Lang | |
| 6,432,146 B1 | 8/2002 | Rondeau | |
| 6,436,153 B2 | 8/2002 | Rondeau | |
| 6,436,436 B1 | 8/2002 | Nguyen | 424/450 |
| 6,440,175 B1 | 8/2002 | Stanley | |
| 6,440,456 B1 | 8/2002 | Nguyen | 424/450 |
| D465,612 S | 11/2002 | Boyd | |
| 6,500,413 B1 | 12/2002 | Kapsner | |
| 6,506,374 B1 | 1/2003 | Pollack | |
| 6,524,614 B2 | 2/2003 | Cannell | 424/401 |
| 6,558,697 B2 | 5/2003 | Cannell | 424/450 |
| 6,703,004 B2 | 3/2004 | Narasimhan | |
| 6,764,523 B2 | 7/2004 | Casperson | |
| 6,770,103 B2 | 8/2004 | Patel | |
| 6,908,491 B2 | 6/2005 | Fischer | |
| 2002/0189034 A1 | 12/2002 | Kitabata | |
| 2003/0028979 A1 | 2/2003 | Duffer | |
| 2003/0051297 A1 | 3/2003 | Patel | 8/405 |
| 2003/0074746 A1 | 4/2003 | Fischer | |
| 2003/0177591 A1 | 9/2003 | Mockli | |
| 2003/0190297 A1 | 10/2003 | Narasimhan | |
| 2003/0233713 A1 | 12/2003 | Quinn | |
| 2004/0011370 A1 | 1/2004 | Vena | |
| 2004/0016064 A1 | 1/2004 | Vena | |
| 2004/0045101 A1 | 3/2004 | Miczewski | |
| 2004/0047672 A1 | 3/2004 | Miczewski | |
| 2004/0047674 A1 | 3/2004 | Geardino | |
| 2004/0098814 A1 | 5/2004 | Au | |
| 2004/0098816 A1 | 5/2004 | Au | |
| 2004/0141931 A1 | 7/2004 | Narasimhan | |
| 2004/0154108 A1 | 8/2004 | Narasimhan | |
| 2005/0125913 A1 | 6/2005 | Narasimhan | 8/405 |

FOREIGN PATENT DOCUMENTS

| | | |
|---|---|---|
| EP | 137178 | 4/1985 |
| EP | 503507 | 9/1992 |
| EP | 821935 | 4/1998 |
| EP | 1366754 | 12/2003 |
| GB | 2132642 | 7/1984 |
| JP | 2138207 | 5/1990 |
| JP | 20011316229 | 11/2001 |
| JP | 2003119116 | 4/2003 |

OTHER PUBLICATIONS

L'Oreal ColorSpa Moisture Actif, No Ammonia Moisturizing Colorant, no date.
U.S. Appl. No. 11/947,680, filed Nov. 29, 2007. Methods, Compositions, and Kit for Coloring Hair. Vena, et al.
U.S. Appl. No. 10/454,405, filed Jun. 4, 2003. Methods, Compositions, and Kit for Coloring Hair. Vena, et al.
Logics, Colorreserve System Color Refresher Revitalizing Conditioner, ingredient labeling. Circa 1993.
1994 Revlon Products Book, p. 49. Colorsilk Color Enhancing Conditioner, 5 Shade Variations. (1) All Pale Blonde & Highlighted Hair. (2) Blondes. (3) All Browns. (4) All Auburns. (5) All Brunettes. Circa Jan. 1994.

* cited by examiner

*Primary Examiner*—Eisa B Elhilo
(74) *Attorney, Agent, or Firm*—Joy S. Goudie

(57) ABSTRACT

An oxidative dye composition comprising one or more oxidative dyes, at least one glyceryl ester, and at least one surfactant, a method for coloring hair, and a method for coloring First Grays and hair that has been chemically processed with a mild, easy to use, hair color.

15 Claims, No Drawings

METHOD AND COMPOSITIONS FOR COLORING HAIR

RELATED APPLICATIONS

This application claims priority from copending U.S. application Ser. No. 11/006,435, filed Dec. 7, 2004 now abandoned, which claims priority from provisional patent application Ser. No. 60/528,746, filed Dec. 11, 2003.

TECHNICAL FIELD

The invention is in the field of hair color compositions and methods for coloring hair.

BACKGROUND OF THE INVENTION

There are a variety of reasons that consumers desire to color their hair. One reason is to completely change hair color. In many cases, consumers first become interested in coloring their hair when their hair begins to gray. The term "First Grays" is usually used to refer to individuals who are just beginning to get gray hair that is noticeable. Generally, individuals having First Grays are those where about ten percent or less of their hair has turned gray. There are few, if any, products that are targeted to consumers interested in treating First Grays. The First Grays consumer is most interested in treating only the gray hair that is present so that it becomes close to its original color. Such consumers are not necessarily interested in coloring all of their hair. The product that best fits the need gaps of the First Grays consumer would be gentle on the hair, quick and easy to use, and would blend away the gray hair without overly processing non-gray hair. Often First Grays consumers view oxidative hair color as too invasive for their needs. They respond by putting off the hair color process completely until their gray hair becomes more pronounced, or oxidatively coloring all of their hair in order to treat the small portion of gray hair that bothers them.

Other types of consumers have a desire for the same type of product that fulfills the need gaps for First Grays. The quick, gentle-to-hair, easy to use, features of such hair color would be very attractive to consumers that use hair relaxers, or consumers who have hair that has been chemically processed via perming, oxidative hair color, and the like. For example, hair relaxers are commonly used among ethnic groups who have kinky hair and desire to straighten it. Hair treated with lye-based relaxers often exhibits a washed out, faded appearance. Relaxer users then want to revitalize the color of their hair but are often reluctant to further assault hair that is already fragile with an oxidative dye procedure.

Consumers who have repeatedly oxidatively dyed or treated their hair with permanent wave processes may also have the same problem. Hair that has been permed may be fragile, dry, and in some cases, damaged. Applying oxidative color to such hair may only further promote damage to the hair. Yet, these consumers often wish to color their hair, and need a product that is mild, yet effective.

In other cases, oxidative hair color users may desire to revitalize the color of the hair. However, for a variety of reasons, such users may be reluctant to undergo another oxidative hair color procedure. Generally, standard oxidative hair color is referred to as "Level 3" hair color. Level 3 hair color involves a process where the melanin fibers of the hair are both bleached or lightened, as well as colored with the oxidative dye. Level 2 hair color, on the other hand, refers to a hair color process where the hair is colored, but not bleached or lightened, with oxidative dyes. Another name for Level 2 hair color is "tone on tone" hair color. It would be most desirable for Level 3 hair color users to have a quick, efficient, mild, process for revitalizing the color of their oxidatively dyed hair using a Level 2 hair color, which is less invasive.

Accordingly, there is a need for a simple, user friendly, fast, and gentle method for coloring hair that is suitable for coloring First Grays, or coloring hair that has been chemically processed. Ideally, this method will provide tones on gray hair, for example, golden tones on brown hair, warm tones on red hair, or ashy tones on black hair.

It is an object of the invention to provide a method and compositions for oxidatively coloring hair in about two to five minutes, preferably about two minutes.

It is a further object of the invention to provide a hair color composition and process suitable for treating First Grays.

It is a further object of the invention to provide a hair color composition and process for coloring hair that has been treated with lye-based hair relaxers.

It is a further object of the invention to provide a hair color composition and process for coloring hair that is gentle, easy to use, fast, and suitable for hair that has been chemically processed such as by permanent waving, Level 3 hair color, and the like.

It is a further object of the invention to provide a hair color composition and process for revitalizing the color of oxidatively colored (Level 3) hair color.

It is a further object of the invention to provide a Level 2 hair color composition and process for revitalizing the color of hair that has been colored with Level 3 hair color.

It is a further object of the invention to provide a hair color composition containing glyceryl esters, preferably lecithin, one or more surfactants, and one or more oxidative dyes.

SUMMARY OF THE INVENTION

The invention is directed to an oxidative dye composition comprising one or more oxidative dyes, at least one glyceryl ester, and at least one surfactant.

The invention is directed to a method for reducing the amount of time required to oxidatively color hair with a mixture of an oxidizing agent composition and an aqueous based oxidative dye composition, comprising including in said mixture at least one glyceryl ester and one or more surfactants.

The invention is also directed to a method for providing color to the hair in about two to four minutes or less comprising treating the hair with a mixture of an oxidizing agent composition and an aqueous based oxidative dye composition wherein the aqueous based oxidative dye composition contains at least one glyceryl ester and one or more surfactants.

The invention is directed to a method for coloring hair in an individual having First Grays, or hair that has been relaxed or otherwise chemically processed, comprising applying to the hair a mixture of an oxidizing agent composition and an aqueous based oxidative dye composition wherein the mixture contains at least one glyceryl ester and one or more surfactants.

The invention is directed to a method for revitalizing the color of hair colored with Level 3 hair color comprising applying to the hair a Level 2 hair color comprised of a mixture of an oxidizing agent composition and an aqueous based oxidative dye composition wherein the mixture contains at least one glyceryl ester and at least one surfactant.

The invention is further directed to a process for revitalizing the color of hair colored with Level 3 hair color comprising applying to the hair a Level 2 hair color comprised of a mixture of an oxidizing agent composition and an aqueous based oxidative dye composition wherein the mixture contains at least one glyceryl ester and at least one surfactant, rinsing the composition from the hair, applying the same composition to the hair again for about two minutes, then rinsing from the hair with water.

DETAILED DESCRIPTION

All percentages stated herein are percentages by weight unless otherwise indicated. The compositions and methods of the invention will be further described herein.

I. The Oxidative Dye Composition

The oxidative dye composition comprises one or more oxidative dyes, at least one glyceryl ester, and at least one surfactant. The oxidative dye composition preferably comprises from about 0.1-99%, preferably about 5-85%, more preferably about 10-75% water, in addition to the oxidative dyes, glyceryl ester, and optional ingredients such as thickeners, fatty acids, preservatives, humectants, and the like.

A. Oxidative Dyes

The oxidative dyes are generally in the form of primary intermediates and couplers. Suggested ranges of primary intermediates are about 0.0001-15%, preferably about 0.0005-12%, more preferably about 0.001-10% by weight of the total composition. Such primary intermediates are well known for use in hair color, and include ortho or para substituted aminophenols or phenylenediamines, such as para-phenylenediamines of the formula:

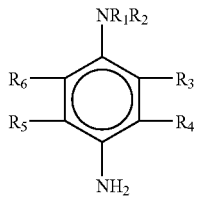

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

The dye composition may comprise one or more color couplers in ranges of about 0.0001-10%, more preferably 0.0005-8%, most preferably 0.001-7% by weight of the total composition. Suitable color couplers include, for example, those having the general formula:

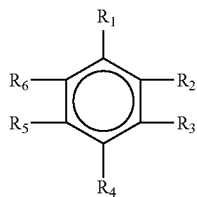

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methylpyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl) amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis (beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Preferred couplers include resorcinol, 1-naphthol, 2-methylresorcinol, m-aminophenol, 2,4-diaminophenoxyethanol, phenyl methylpyrazolone, their salts, or mixtures.

Preferably the oxidative dye composition comprises one or more primary intermediates and one or more color couplers in the amounts set forth.

B. Glyceryl Esters

The oxidative dye composition comprises at one glyceryl ester. Preferably, the glyceryl ester is present in amounts ranging from about 0.001-45%, preferably about 0.005-40%, more preferably about 0.5-35% by weight of the total composition. Suitable glyceryl esters are generally defined as fatty acid mono-, di- or triglycerides which may be modified by reaction with other alcohols and the like. Also included within the category of glyceryl esters are fatty acid esters of polyglycerin, and the complex dehydration product of glycerin. Examples of glyceryl esters suitable for use in the composition are set forth on pages 1680-1683 of the *C.T.F.A. International Cosmetic Ingredient Dictionary and Handbook*, Eighth Edition, 2000, which is hereby incorporated by reference in its entirety.

Further examples of suitable glyceryl esters include acetylated glycerides, or acetylated hydrogenated glycerides from cottonseed, lard, tallow, vegetable, palm kernel, for example, acetylated hydrogenated cottonseed glyceride, acetylated hydrogenated lard glyceride, acetyled lard glyceride, and so on.

Also suitable are mono-, di-, or triglycerides formed by the reaction of glycerin with one or more carboxylic acids, which may be fatty acids. Typically such ingredients are formed by the reaction of a $C_{1-35}$ carboxylic acid, or a $C_{6-22}$ fatty acid with glycerin to form a mono- di, or triglyceride depending on the number of carboxylic acid acids used. Examples of such ingredients include glyceryl adipate, arachidate, arachidonate, behenate, behenate/eicosadioate, caprate, caprylate, caprylate/caprate, citrate, lactate, cocoate, diarachidate, dibehenate, dierucate, dihydroxystearate, diisopalmitate, diisostearate, dilaurate, dilinoeate, dimyristate, dipalmitate, dipalmitoleate, diricinoleate, distearate, erucate, isopalmitate, isostearate, lanolate, laurate, linoleate, linolenate, myristate, oleate, palmitate, ricinoleate, sesquioleate, stearate, tallowate, and the like.

Also suitable are alkylene glycols or polyalkylene glycols of mono-, di-, and triglycerides including PEG glycerides where the number of repeating ethylene glycol units ranges from about 3 to 250. Examples of such ingredients include $PEG_{2-200}$ glyceryl triisostearate, trioleate, tallowate, sesquioleate, ricinoleate, oleate, laurate, isostearate, stearate, cocoate, and the like.

Also suitable are carboxylic acid, preferably fatty carboxylic acid, esters of polyglycerin. These esters of polyglycerin are generally formed by reacting a $C_{1-35}$ carboxylic acid, preferably a $C_{6-22}$ fatty acid with polyglycerin, or glycerin having from about 2 to 200, preferably about 2-20 repeating units. Examples of such ingredients include polyglyceryl$_{2-200}$ diisostearate, cocoate, caprate, stearate, laurate, myristate, oleate, caprate, dicaprate, dialurate, dipalmitate, heptaoleate, distearate, palmitate, and the like.

Also suitable are phospholipids, including but not limited to lecithin. Lecithin is widely available from a variety of commercial sources and is a naturally occurring mixture of the diglycerides of stearic, palmitic, and oleic acids linked to the choline ester of phosphoric acid, and is also referred to as egg yolk lecithin, soybean phospholipid, or soybean lecithin.

C. Association Structures

Without being bound by this explanation, it is believed that the beneficial properties of the claimed composition and process may, in some cases, be due to the formation of association structures between the glyceryl ester and the surfactants present. The compositions and methods of the invention, however, are more broadly directed to the case where the at least one glyceryl ester and one or more surfactants may be present, and such compositions may or may not contain association structures. Particularly in the case where glyceryl ester that is used is lecithin, association structures will form in the composition. However, this may not be the case with one or more of the other types of glyceryl esters that may be used in the composition.

Association structures are a type of liquid crystalline state that occurs when the molecules present in a composition exhibit intermediate stages of order. More specifically, association structures are formed when certain amphiphilic ingredients present in a polar solvent-containing composition align in a head-to-head/tail-to-tail configuration therein to form certain types of molecular arrangements. By "head-to-head/tail-to-tail" is meant that the hydrophilic portions of the amphiphilic ingredients are attracted to each other and the lipophilic portions are also attracted to each other such that the amphiphilic ingredients will form a certain molecular order within the composition, which is somewhere between the completely disordered liquid state and the completely ordered solid state. In the case where such association structures may be formed, the compositions of the invention are preferably in the form of about 0.1-95%, preferably about 0.5-85%, more preferably about 1-80% of association structures, meaning that that percentage of the total composition is in the form of association structures.

When the amphiphilic ingredients are oriented in such a manner, certain active ingredients may be found within the composition. For example, the oxidative dyes may be enclosed, or solvated, within the molecular arrangements formed by the oriented molecules. In the case where the glyceryl ester and one or more surfactants present form association structures in the composition, they may be of various types, including those described below.

1. Liquid Crystals

Liquid crystalline phases are generally named according to their degree of molecular ordering. The general stages of order are (1) isotropic—random ordering of molecules (2) nematic ordering—molecules are orientationally ordered, or in a generally parallel configuration in one dimension, (3) smectic ordering—molecules are orientationally ordered in two dimensions, and (4) crystal—completely oriented solid state. Smectic liquid crystals are given the designation "S" and can be further classified into subcategories A-H based upon their degree of ordering. For example, the smectic B phase (SB) is a disordered crystal where the molecules are arranged in hexagonal arrangement and the positions of the hexagonal nets within each layer repeat in a regular manner throughout the phase. The liquid crystal association structures that may be found in certain compositions according to the invention may be in the rod or vesicle form and exhibit a generally lamellar configuration It is possible that nematic liquid crystals may be formed in the compositions of the invention. Nematic liquid crystals are referred to by the designation "N". The nematic liquid crystals may be lyotropic. Obviously excluded are the isotropic and crystalline states which represent the disordered molecular orientation and the completely molecularly ordered state respectively.

As discussed above, the liquid crystals, if present, may be formed by the combination of certain amphiphilic surfactants in a polar solvent. Suitable amphiphilic surfactants and polar solvents will be further discussed below.

2. Micelles

The association structures, if present, may be in the form of micelles, which are assemblies of amphiphilic molecules whose polar head groups are exposed to water and whose aliphatic or lipophilic side chains are oriented toward a hydrophobic interior. More particularly, in an emulsion having a dispersed lipophilic phase and an aqueous continuous phase, the lipophilic portion of the amphiphilic molecule will orient at the surface of the dispersed oil droplets and the hydrophilic portion will orient toward the continuous water phase.

Reverse micelles are found in water in oil emulsions and occur when the polar head groups of the amphiphilic material orient toward the dispersed water droplets and the lipophilic portions toward the continuous lipophilic phase.

In the case where the oxidative dye composition is in the form of an emulsion, the emulsion may be a microemulsion where the dispersed phase droplets are very small, generally from about 100 to 1500, preferably 200 to 1000, more preferably 250 to 700 Angstroms (Å).

3. Other Association Structures

It is possible that other types of association structures may be found in certain embodiments of the invention, such as liposomes, vesicles, and the like. Liposomes are microscopic spherical vesicles formed when phospholipids are hydrated in a polar solvent such as water.

4. Formation and Benefit of Association Structures

The association structures in the oxidative dye composition, if present, may be formed when certain amounts of glyceryl ester, preferably lecithin, and one or more amphiphilic surfactants are combined with water either alone or in combination with one or more other polar solvents. In order to optimize the formation of association structures, certain other lipophilic ingredients may be added to the mixture.

D. Surfactants

The composition contains at least one surfactant. In the case where association structures are formed in the composition, the surfactant is, ideally, one that is capable of forming association structures in water or polar solvents at a temperature ranging from about 20 to 60° C., preferably about 25 to 40° C. In the case where the composition may not form association structures, the surfactants are present to stabilize or emulsify the composition, or otherwise provide a beneficial effect.

The surfactant may be anionic, cationic, nonionic, amphoteric, or zwitterionic. The composition may contain more than one surfactant. Generally the amount of the surfactant may preferably range from about 0.001-50%, preferably about 0.005-45%, more preferably about 0.01-40% by weight of the total composition. The surfactants include those set forth below.

1. Nonionic Surfactants

A variety of nonionic surface active agents may be used in the claimed compositions. Preferably, such surface active agents HLB (hydrophile/lipophile balance) of about 12-20, more preferably about 13-16. Nonlimiting examples of nonionic surfactants include:

(a). Alkoxylated Alcohols

Suitable alkoxylated alcohols include ethers formed from the reaction of an aliphatic, aromatic, or heterocyclic alcohol with an alkylene oxide, generally ethylene or propylene oxide. Preferably, the alcohol is an aliphatic alcohol, more preferably a fatty alcohol having 10-22 carbon atoms; and the alkylene oxide is ethylene oxide. Examples of preferred alkoxylated alcohols include steareth, ceteth, ceteareth, beheneth, and the like, having from 1 to 200 repeating ethylene oxide units, as well as PEG derivatives of fatty acids such as PEG dioleate, PEG distearate, PEG isostearate, and so on.

(b). Sorbitan Derivatives

Suitable sorbitan derivatives are esters or ethers or sorbitan, which is a heterocyclic ether formed by the dehydration of sorbitol. Sorbitan may be derivatized by ethoxylation and/or esterification of the hydroxyl groups. Suitable acids used for esterification include $C_{1-30}$ acids, more preferably, fatty acids having 6-22 carbon atoms. Examples of suitable sorbitan derivatives include PEG derivatives of sorbitan wherein the number of repeating ethylene oxide units ranges from 2 to 200, such as PEG sorbitan beeswax, glyceryl/sorbitol/oleate/hydroxystearate, PEG sorbitan cocoate, PEG sorbitan diisostearate, PEG sorbitan isostearate, PEG sorbitan lanolate, PEG sorbitan laurate, PEG sorbitan oleate, PEG sorbitan palmitate, PEG sorbitan perisostearate, PEG sorbitan peroleate, PEG sorbitan stearate, PEG sorbitan tetraoleate, PEG sorbitan tetrastearate, PEG sorbitan triisostearate; Polysorbates such as Polysorbate 20-85, Polysorbate 80 acetate; and sorbitan esters such as sorbitan caprylate, cocoate, diisostearate, dioleate, distearate, isostearate, laurate, oleate, olivate, palmitate, sesquiisostearate, sesquioleate, sesquistearate, stearate, triisostearate, trioleate and the like.

(c). Glyceryl Ethers

Also suitable are linear or branched ethers of polyglycerol having the general formula:

$$R\text{-}(Gly)_n\text{-}OH$$

wherein n is 1-10 and R is a straight or branched, saturated or unsaturated alkyl having 6 to 30 carbon atoms, and Gly is the glycerol residue. Examples of suitable polyglyceryl derivatives include polyglyceryl decaoleates, polyglyceryl caprates, polyglyceryl diisostearates, polyglyceryl distearates, polyglyceryl isopalmitates, polyglyceryl laurates, and the like.

(d). Dialkyl Sulfoxides

Also suitable are long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(e). Polyethylene Oxide Condensates of Alkyl Phenols

Suitable condensates include the condensation products of alkyl phenols having an alkyl group of 6 to 20 carbon atoms with ethylene oxide being present in amounts of about 10 to 60 moles of ethylene oxide per mole of alkyl phenol.

(f). Condensation Product of Ethylene Diamine

Examples of suitable condensation products of ethylene diamine include products of ethylene oxide with the reaction product of propylene oxide and ethylene diamine.

(g). Long Chain Tertiary Amine Oxides

Preferred long chain tertiary amine oxides include those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(h). Long Chain Tertiary Phosphine Oxides

Suitable long chain tertiary phosphine oxides include those corresponding to the general formula:

$$RR_1R_2PO$$

wherein R contains an alkyl, alkenyl, or monohydroxyalkyl radical having 8 to 18 carbon atoms, from 0-10 ethylene oxide moieties and 0 or 1 glyceryl moiety, and $R_2$ and $R_3$ are each alkyl or monohydroxyalkyl group containing from about 1 to 3 carbon atoms.

(i). Polyhydroxyl Fatty Acid Amides

Examples of $C_{10-18}$ is alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

(j). Alkyl Polysaccharides

Suitable nonionic surfactants are alkyl polysaccharides, or alkyl glycosides, disclosed in U.S. Pat. Nos. 5,716,418 and 5,756,079, both of which are hereby incorporated by reference. These alkylglycosides have the general formula:

$$R_1-O-(R_2O)_t-(G)_n-H$$

wherein $R_1$ is a linear or branched alkyl or alkenyl radical having 12 to 30 carbon atoms, $R_2$ is a $C_{2-4}$ alkylene, (G) is an anhydroglucose unit, t is a number between 0 and 10, preferably 0 to 4, and n is a number from about 1 to 15. Examples of such alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on. Certain polyglycosides having the above formula are sold by Henkel Corporation under the tradenames APG 300, APG 350, APG 500, APG 550, APG 625, or the tradename Planteren, e.g. Planteren 300, 600, 1200, 2000, and so on.

2. Anionic Surfactants

Also suitable for use in the compositions of the invention are one or more anionic surfactants.

(a). Alkyl Sulfates

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

(b). Fatty Acids Esterified with Isethionic Acid

Also suitable as anionic surfactants are reaction products of fatty acids esterified with isethionic acid and neutralized with sodium hydroxide. The fatty acids may be derived from coconut oil or other similar vegetable or animal derived oils that contain fatty acids.

(c). Succinates or Succinimates

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

(d). Olefin Sulfonates

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

(e). Soaps

Other suitable anionic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts. Soaps may also form through the reaction of one or more fatty acids with mono-, di-, or trialkanolamines.

(f). N-acyl Amino Acids

Still another class of anionic surfactants include N-acyl amino acid surfactants and salts thereof (alkali, alkaline earth, and ammonium salts) having the formula:

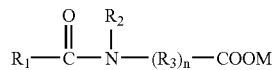

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

3. Cationic, Amphoteric, or Zwitterionic Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

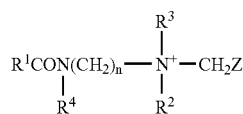

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium. cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

or iminodialkanoates of the formula:

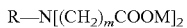

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. The general formula for such surfactants is:

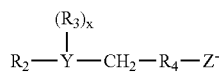

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionic surfactants include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like.

E. Other Ingredients

1. Polar Solvents

A variety of polar solvents other than water may be used in the oxidative dye composition, such as mono-, di-, or polyhydric alcohols, and similar water soluble ingredients. Preferably, the oxidative compositions comprise from about 0.1-99.9%, preferably about 5-95%, more preferably about 10-90% by weight of the total composition of polar solvent in addition to water. Examples of such table non-aqueous Suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like. Many of these types of alcohols also serve also serve as penetration enhancers, meaning that they enhance penetration of the dyes into the hair shaft by virtue of their tendency to act as humectants and swell the hair shaft. Ethoxydiglycol is a particularly good penetration enhancer.

In the preferred embodiment of the invention the composition comprises water in addition to one or more polar solvents, which are dihydric alcohols. In the preferred compositions, about 0.001-20%, preferably about 0.005-10%, more preferably about 0.001-8% by weight of the total composition comprises a non-aqueous polar solvent.

2. Lipophilic Materials

Certain additional lipophilic materials may be used in addition to the surfactants and glyceryl ester. If present, such lipophilic materials may range from about 0.001-25% by weight of the total composition. Preferred lipophilic materials include:

(a). Fatty Acids

The oxidative dye composition may contain one or more fatty acids. Suitable fatty acids include carboxylic acids having the general formula R—COOH wherein R is a straight or branched chain, saturated or unsaturated alkyl having about 7 to 30 carbon atoms. Suggested ranges of fatty acid, if present, are about 0.01-25%, preferably about 0.05-20%, preferably about 0.1-15% by weight of the total composition. Suitable fatty acids include oleic, palmitic, arachidic, arachidonic, behenic, capric, caproic, capryllic, coconut, tallow, lauric, linoleic, linolenic, myristic, pelargonic, ricinoleic, stearic, undecylenic, and so on. Particularly preferred is oleic acid, an unsaturated fatty carboxylic acid. The fatty acids aid in the formation of liquid crystals.

(b). Fatty Alcohols

One or more fatty alcohols may also be included in the composition. Fatty alcohols exhibit the general formula R—CH$_2$OH where R is a straight or branched chain, saturated or unsaturated alkyl having about 7 to 30 carbon atoms. Suggested ranges of fatty alcohols, if present, are about 0.001-15%, preferably about 0.005-10%, preferably about 0.01-8% by weight of the total composition. Examples of suitable fatty alcohols include arachidyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, cetyl alcohol, coconut alcohol, decyl alcohol, palm alcohol, lauryl alcohol, myristyl alcohol, oleyl alcohol, tallow alcohol, tridecyl alcohol, and mixtures thereof. Particularly preferred is oleyl alcohol, cetearyl alcohol, and mixtures thereof.

3. Other Ingredients (a). Thickening Agents

The composition may also contain one or more agents that will provide a thickening, or viscosity increasing, effect to the compositions. Examples of such thickening agents include synthetic metal silicates, acrylate copolymers, associative thickeners, cellulose polymers, and the like. Particularly preferred are alkali metal or alkaline earth metal silicates. Suitable alkali metals or alkaline earth metals include sodium, potassium, magnesium, lithium, and the like either alone or in combination with aluminum. Suggested ranges are from about 0.001-20%, preferably about 0.005-15%, preferably about 0.01-12% by weight of the total composition. Particularly preferred are cellulose or alkyl- or hydroxyalkyl cellulose derivatives such as ethyl cellulose, hydroxypropylethylcellulose, and the like.

(b). Preservatives

The composition may also contain one or more preservatives. Suggested ranges are about 0.0001-8%, preferably 0.0005-7%, more preferably about 0.001-5% by weight of the total composition. Suitable preservatives include methyl, ethyl, and propyl paraben, hydantoins, and the like.

(c). Chelating Agents

The composition may also contain 0.0001-5%, preferably 0.0005-3%, more preferably 0.001-2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

(d). pH Adjusters

It may also be desirable to add small amounts of acids or bases to adjust the pH of the composition to the desired pH range of 7.1 to 11. Suitable acids include hydrochloric acid, phosphoric acid, erythorbic acid, and the like. Suitable bases include sodium hydroxide, potassium hydroxide, and the like. Also suitable are primary, secondary, or tertiary amines or derivative thereof such as aminomethyl propanol, monoethanolamine, and the like. Suggested ranges of pH adjusters are from about 0.00001-8%, preferably about 0.00005-6%, more preferably about 0.0001-5% by weight of the total composition.

Preferably, the oxidative dye compositions of the invention are in the form of a shampoo composition comprising one or more anionic surfactants. The consumer can simply apply the composition to the hair as a normal shampoo is applied to hair. If desired, the oxidative dye composition and the developer composition may be free of ammonia compounds such as ammonium hydroxide, ammonium sulfate, and the like; or contain these compounds in very small amounts, e.g. less than 1% by weight, or preferably less than 0.5% by weight. The term "free of" means that the ammonia compounds are not intentionally added to the composition.

II. The Aqueous Oxidizing Agent Composition

The oxidative dye compositions are combined with an aqueous oxidizing agent, or developer composition prior to application to the hair. The developer mixture in its simplest form is an aqueous solution of hydrogen peroxide. Preferably the developer composition comprises 1-99%, preferably 10-99%, more preferably 60-97% of water, and about 5-20%, preferably 6-15%, more preferably 7-10% by weight of the total developer composition of hydrogen peroxide. Developer compositions are generally sold in the form of 10, 20, 25, and 30 volume hydrogen peroxide. The 20 volume hydrogen peroxide developer composition comprises 6% by weight of hydrogen peroxide. The 25 volume hydrogen peroxide developer composition contains about 7.5% of hydrogen peroxide and the 30 volume hydrogen peroxide developer composition about 9%, with all weight percentages by weight of the total composition of hydrogen peroxide. In the most preferred embodiment of the invention, the developer composition used has a comparatively low concentration of hydrogen peroxide, specifically about 10 volume or lower. Preferably, the aqueous oxidizing agent composition comprises from about 5 to about 20 volume of hydrogen peroxide. If desired, the developer composition may contain a variety of other ingredients that enhance the aesthetic properties and contribute to more efficient coloring of hair. Preferred developer compositions for use with the oxidative dye composition and in the method of the invention, when combined with the oxidative dye composition, form a composition very similar in consistency to a shampoo. Suggested developer compositions preferably comprise:

0.5-25% hydrogen peroxide,
0.1-10% of a conditioner,
0.01-5% of a thickener, and
1-99% water.

A. Conditioners

The developer composition may contain one or more conditioners that exert a conditioning effect on hair. Examples of suitable conditioning ingredients include, but are not limited to those set forth below.

1. Cationic Silicones

As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula, where the ratio of D to T units, if present, are greater than about 80 D units to 1 T unit:

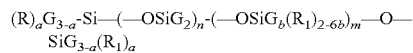

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from 2 to 8 and L is selected from the groups:

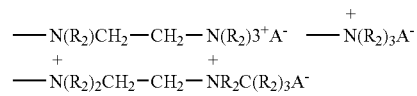

in which $R_2$ is selected from the group consisting of H, phenyl, benzyl, a saturated hydrocarbon radical, and is preferably an alkyl radical containing 1-20 carbon atoms; and A— is a halide, methylsulfate, or tosylate ion.

Preferably the dye mixture comprises one or more conditioners that exert a conditioning effect on hair. A variety of conditioners are suitable including cationic polymers, oily conditioning agents, fatty alcohols, proteins, and so on. A combined total weight of conditioners ranges from about 0.1-25%, preferably 0.5-20%, more preferably 1-15% by weight of the total composition.

2. Cationic Polymers

A variety of cationic polymers are suitable such as quaternary derivatives of cellulose ethers or guar derivatives, copolymers of vinylpyrrolidone, polymers of dimethyldiallyl ammonium chloride, acrylic or methacrylic polymers, quaternary ammonium polymers, and the like.

(a) Quaternary Derivatives of Cellulose

Examples of quaternary derivatives of cellulose ethers are polymers sold under the tradename JR-125, JR-400, JR-30M. Suitable guar derivatives include guar hydroxypropyl trimonium chloride.

(b) Copolymers of Vinylpyrrolidone

Copolymers of vinylpyrrolidone having monomer units of the formula:

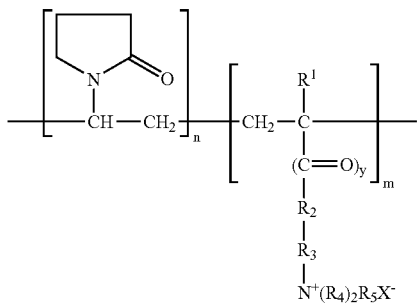

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

c) Polymers of Dimethyldiallylammonium Chloride

Homopolymers of dimethyldiallylammonium chloride or copolymers of dimethyldiallylammonium chloride and acrylamide are also suitable. Such compounds are sold under the tradename MERQUAT by Calgon.

(d) Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use.

(e) Polymeric Quaternary Ammonium Salts

Also suitable are polymeric quaternary ammonium salts of cellulose and other polymers, including but not limited to Polyquaternium 10, 28 31, 33, 34, 35, 36, 37, and 39.

(f) Diquaternary Polydimethylsiloxanes

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

Particularly preferred are conditioners Polyquaternium 10 and Polyquaternium 28. Polyquaternium-10 is the polymeric quaternary ammonium salt of hydroxyethyl cellulose reacted with trimethyl ammonium substituted epoxide. Polyquaternium-28 is the polymeric quaternary ammonium salt consisting of vinyl pyrrolidone and dimethylaminopropyl methacrylamide monomers.

(g) Oily Conditioning Agents

Also suitable are a variety of oily materials that provide good conditioning effect to hair. Suitable oils are liquid at room temperature and may comprise esters, hydrocarbons, and the like. Preferably the composition comprises 0.001-20%, more preferably 0.005-15%, most preferably 0.01-10% by weight of the total composition of such oils. Particularly preferred oily conditioning agents are oils extracted from vegetable sources, specifically meadowfoam seed oil.

(h) Nonionic Silicones

Also suitable as conditioning agents are one or more silicones. Suitable silicone hair conditioning agents include volatile or nonvolatile nonionic silicone fluids, silicone resins, and silicone semi-solids or solids.

Volatile silicones are linear or cyclic silicones having a measureable vapor pressure, which is defined as a vapor pressure of at least 2 mm. of mercury at 20° C. Examples of volatile silicones are cyclic silicones having the general formula:

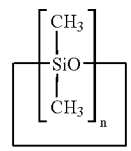

where n=3-7.

Also, linear volatile silicones that may be used in the compositions of the invention have the general formula:

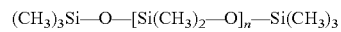

where n=0-7, preferably 0-5.

Also suitable are nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

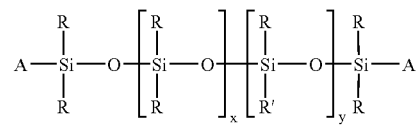

wherein R and R' are each independently alkyl, aryl, or an alkyl substituted with one or more amino groups, and x and y are each independently 0-100,000, with the proviso that x+y equals at least one and A is siloxy endcap unit. Preferred is where A is methyl, R is methyl, and R' is an alkyl substituted with at least two amino groups, most preferably an amine-functional silicone having the formula:

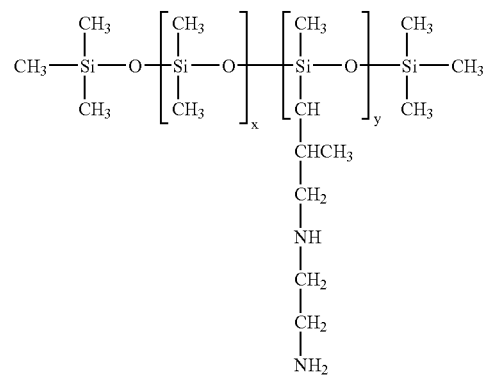

which is known by the CTFA name trimethylsilylamodimethicone.

Another type of silicone conditioning agent is a silicone polymer having the following general formula:

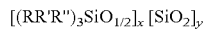

$[(RR'R'')_3SiO_{1/2}]_x [SiO_2]_y$ wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups, which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename Dow Corning 749 Fluid, which is a blend of about 40-60% volatile silicone and 40-60% trimethylsiloxy silicate (trimethylated silica). The fluid has a viscosity of 200-700 centipoise at 25° C., a specific gravity of 1.00 to 1.10 at 25° C., and a refractive index of 1.40-1.41.

2. Thickeners

The developer composition may contain one or more thickeners that assist in maintaining an increased viscosity of the final composition resulting from mixture of the hair dye and the developer compositions. The amount of thickening agent if present is about 0.001-5%, preferably about 0.005-4%, more preferably about 0.005-3% by weight of the total composition.

A variety of thickening agents are suitable including those mentioned above with respect to the oxidative dye composition, in addition to low melting point waxes, carboxyvinyl polymers, and the like. Also suitable are a variety of water soluble anionic thickening polymers such as those disclosed in U.S. Pat. No. 4,240,450, which is hereby incorporated by reference. Suggested ranges of such polymers are about 0.01-5%, preferably 0.05-4%, more preferably 0.1-3% by weight of the total developer composition. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

3. Other Ingredients (a). Nonionic Surfactants

The developer composition may contain one or more nonionic surfactants. Suitable nonionic surfactants are the same as those mentioned above with respect to the oxidative dye composition and in the same amount.

(b). Chelating Agents

The developer composition may contain one or more chelating agents as described herein with respect to the oxidative dye composition, and in the same ranges by weight.

III. The Method

The invention is directed to a method for reducing the amount of time required to oxidatively color hair, and a method for providing oxidative color to the hair in about two to four minutes, preferably about two minutes. The invention is also directed to a method for coloring First Grays, revitalizing the color of hair colored with Level 3 hair color, and coloring hair that has otherwise been chemically processed via perming, relaxer treatments, or oxidative dyes.

When the oxidative dye and developer compositions of the invention are mixed, the mixture is capable of providing permanent oxidative color to hair in about two to four minutes.

Typically, the oxidative dye composition and developer composition are combined in about a one to one ratio and immediately applied to wet hair. Both compositions are formulated so that when mixed they provide a shampoo-like composition that is easy to apply to wet or dry hair. It is noted that this is a distinct point of difference between traditional oxidative hair color procedures and the process of the invention. Specifically, in traditional hair color procedures, the mixture of the oxidative dye composition and developer is applied to dry hair. However, in the claimed method, the mixture of the oxidative dye composition and the developer may applied to wet or dry hair. Application of the mixture to wet hair facilitates use of the composition and method as part of normal cleansing routines such as showers or baths. In the preferred embodiment the oxidative dye composition is in the form of a shampoo-like composition that the consumer combines with the developer immediately prior to use and uses like a normal shampoo. The hair is shampooed with this mixture in the normal manner for at least two minutes, then rinsed with water. If desired a hair conditioner can be applied after the mixture is rinsed from the hair. The resulting method applies a Level 2 color to the hair that is equivalent to the color applied to hair with the traditional Level 3 oxidative hair coloring procedures and products.

The compositions and methods of the invention are excellent in blending away gray hair, revitalizing the color of chemically processed hair, and providing color in a very short period of time. In addition, the mixture is very mild to hair so it can be used on hair that may be damaged, dry, or brittle, without adverse effects.

The invention will be further described in connection with the following examples, which are set forth for the purpose of illustration only.

EXAMPLE 1

Oxidative hair color compositions according to the invention were made as follows:

| Ingredient | A (Medium Brown) w/o lecithin) | B (Medium Brown) | C (Red Brown) | D (w/o dye & w/ lecithin) | E (w/o dye, w/o lecithin) |
|---|---|---|---|---|---|
| | w/w % | | | | |
| Water | QS | QS | QS | QS | QS |
| Ethoxydiglycol | 5.00 | 5.00 | 5.00 | 5.00 | 5.00 |
| Disodium EDTA | 0.50 | 0.50 | 0.50 | — | 0.50 |
| Erythorbic acid | 0.50 | 0.50 | 0.50 | 0.50 | 0.50 |
| Sodium sulfite | — | — | — | — | — |
| P-phenylenediamine | 3.50 | 3.50 | 3.00 | — | — |
| P-aminophenol | 0.91 | 0.91 | 0.60 | — | — |
| M-aminophenol | 0.50 | 0.50 | 1.10 | — | — |
| Phenyl methyl pyrazolone | 0.25 | 0.25 | — | — | — |
| 4-amino-2-hydroxytoluene | — | — | 1.40 | — | — |
| Lecithin | — | 5.00 | 5.00 | 5.00 | — |
| Hydroxypropyl methylcellulose | 0.30 | 0.30 | 0.30 | 0.30 | 0.30 |
| Tetrasodium EDTA | 0.50 | 0.50 | 0.50 | 0.50 | 0.50 |
| Sodium lauryl sulfate (30%) | 10.00 | 10.00 | 10.00 | 10.00 | 10.00 |
| Sodium laureth sulfate (28%) | 20.00 | 20.00 | 20.00 | 20.00 | 20.00 |
| Lauramide DEA (82-86%) | 2.00 | 2.00 | 2.00 | 2.00 | 2.00 |
| Cocamidopropyl betaine (35%) | 4.00 | 4.00 | 4.00 | 4.00 | 4.00 |
| Oleic acid | 9.38 | 9.38 | 9.38 | 11.20 | 11.20 |
| Ethanolamine | 3.60 | 3.60 | 3.60 | 6.30 | 6.30 |
| Fragrance oil | 0.50 | 0.50 | 0.50 | 0.50 | 0.50 |

The compositions were prepared by combining the ingredients and mixing well. When a small amount was combined with water, the mixture formed a shampoo-like lather.

EXAMPLE 2

Aqueous oxidizing agent or developer compositions were made as follows:

| Ingredient | 10 Volume | 20 Volume |
|---|---|---|
| | w/w % | |
| Water | QS | QS |
| Disodium EDTA | 0.02 | 0.02 |
| Acrylates C10-30 alkyl acrylate crosspolymer | 2.00 | 2.00 |
| Tetrasodium EDTA | 0.68 | 0.68 |
| Triethanolamine | 0.70 | 0.70 |
| Disodium phosphate | 0.01 | 0.01 |
| Metaphosphoric acid | 0.05 | 0.05 |
| Hydrogen peroxide (35% aqueous solution) | 9.00 | 18.00 |

The compositions were prepared by combining the ingredients and mixing well. The compositions were clear liquids.

EXAMPLE 3

Standard oxidative hair dye compositions not according to the invention were made according to the following formulas:

| Ingredient % by weight | Medium Brown | Red Brown |
|---|---|---|
| Water | QS | QS |
| Sodium sulfite | 1.00 | 1.00 |
| Erythorbic acid | 0.20 | 0.20 |
| Oleic acid | 13.00 | 13.00 |
| Isopropyl alcohol | 5.00 | 7.00 |
| Potassium cocoyl hydrolyzed collagen | 4.50 | 4.50 |
| Lauramide MEA | 3.00 | 3.00 |
| Sodium laureth sulfate (28% aqueous solution) | 6.70 | 6.70 |
| PEG-2 cocamine | 4.50 | 4.50 |
| Tetrasodium EDTA | 0.30 | 0.30 |
| Limanthes alba (meadowfoam) seed oil | 0.01 | 0.01 |
| Oleyl alcohol | 0.01 | 0.01 |
| Laneth-5 | 0.80 | 0.80 |
| Ethanolamine | 8.00 | 8.00 |
| P-Phenylenediamine | 3.50 | 3.00 |
| Phenyl methyl pyrazolone | 0.25 | — |
| 4-amino-2-hydroxytoluene | — | 1.40 |
| P-aminophenol | 0.91 | 0.60 |
| M-aminophenol | 0.50 | 1.10 |
| Hypnea musciformis extract, gellidiela acerose extract, sargassum filipendule extract, sorbitol | 0.01 | 0.01 |
| Sodium benzotriazolyl butylphenol sulfonate, buteth-3, tributyl citrate, wheat amino acids | 0.01 | 0.01 |
| Wheat amino acids | 1.00 | 1.00 |
| Fragrance | 1.00 | 1.00 |

The compositions were prepared by combining the ingredients and mixing well.

EXAMPLE 4

A wash out study was conducted on 95% gray hair swatches. One set of swatches was colored with a mixture of 1.0 parts of the medium brown oxidative hair dye of Example 3 and 1.0 pans of the 10 volume hydrogen peroxide composition of Example 2 for 2 minutes. The mixture was rinsed from the swatches with water. A second set of swatches was colored with a mixture of 1.0 part of the medium brown shampoo A in Example 1 and 1.0 parts of the 10 volume hydrogen peroxide composition of Example 2 for 2 minutes. The mixture was rinsed from the swatches with water. A third set of swatches was colored with a mixture of 1.0 parts of the medium brown shampoo B in Example 1 and 1.0 parts of the 10 volume hydrogen peroxide composition of Example 2 for 2 minutes, then rinsed well with water. The chromaticity of the swatches was measured and compared using the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

|  | L | A | b | ΔL | ΔE |
| --- | --- | --- | --- | --- | --- |
| Medium Brown Oxidative Hair Dye | 45.05 | 4.48 | 9.08 |  |  |
| Medium Brown Shampoo Composition of the Invention Without Lecithin | 40.12 | 3.90 | 6.65 | −4.93 | 5.53 |
| Medium Brown Shampoo Composition of the Invention With Lecithin | 35.05 | 4.28 | 5.46 | −10.00 | 10.63 |

The above results illustrate that when the shampoo composition with lecithin is used in the dyeing process, more color is deposited on the hair when compared to the same shampoo composition without Lecithin and a normal hair dye. This is evidenced by the negative numbers in the ΔL column, which mean that the hair swatches became darker. The total change in color when the shampoo was used was significantly greater than a standard oxidation hair color base.

EXAMPLE 5

Color deposit between the oxidative dye composition of the invention in red/brown shades (Formula C, Example 1) and a standard oxidative hair dye in the red/brown shade (Example 3) on 95% gray hair swatches was compared. Swatches were colored with a mixture of 1.0 parts of the oxidative hair dye of Example 1, Formula C) and 1.0 part of the 10 Volume developer of Example 2 for 2 minutes. The mixtures were rinsed from the swatches with water. A second set of swatches was colored with a mixture of 1.0 part of the red/brown oxidative hair dyes in Example 3, and 1.0 parts of the 10 volume hydrogen peroxide composition in Example 2 for 2 minutes. The mixtures were rinsed from the swatches with water. The chromaticity of the swatches was measured and compared using the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

|  | L | A | b | ΔL | ΔE |
| --- | --- | --- | --- | --- | --- |
| Red/Brown Oxidative Hair Dye | 45.99 | 9.38 | 7.58 | — | — |
| Red Brown Shampoo Composition of Invention With Lecithin | 34.89 | 7.1 | 6.36 | −11.1 | 11.4 |

The above results show that the oxidative dye composition of the invention exhibits substantially improved color deposit in the red/brown shade. Specifically, the negative numbers in the ΔL column means that the colored swatch was darker than the swatch colored with the standard red/brown oxidative dye of Example 3 to which it is compared.

EXAMPLE 6

The total and free alkalinity of standard oxidative dye compositions and the oxidative dye composition of the invention were compared. Free alkalinity is the amount of alkalizing agent present that has not reacted with any of the other ingredients in the composition in situ to form soap or other reaction products. Total alkalinity is the total amount of alkalizing agent present which is a combination of the free alkalinity and the bound, or reacted alkalinity, the latter being the amount of alkalizing agent reacted with other ingredients in the composition in situ to form soap or other reaction products. Free alkalinity has an impact on penetration of oxidative dyes and peroxide into the hair shaft. Generally, the greater the free alkalinity concentration, the more efficient the composition will be in penetrating the hair shaft (within certain limits). Without being bound by this explanation, it is believed that the free alkalizing agent causes the hair cuticle to swell and permits penetration of the ingredients in the oxidizing agent composition. Total and free alkalinity for the following oxidative dye compositions were calculated:

| Oxidative Dye | Total Alkalinity (meq/gm) | Free Alkalinity (meq/gm) |
| --- | --- | --- |
| Medium Brown Oxidative Hair Dye from Example 3 | 1.402 | 0.909 |
| Formula D, Example 1 | 0.990 | 0.550 |

The formula D was chosen for comparative purposes because it has more free alkalinity compared to other shades. The above results show that the invention composition without dyes has a lower total and free alkalinity concentration than is found in the standard oxidizing agent compositions. However, the oxidative dye compositions are just as, if not more, efficient in dyeing hair than the standard oxidative dye compositions as demonstrated in the other Examples.

EXAMPLE 7

Hair lightening studies were conducted using the compositions of the invention and L'Oréal Color Spa Moisture Actif Hair Color #52. The ingredient labeling of the L'Oréal product is reproduced below:

No-Ammonia Color Gel ingredients: Water, Trideceth-12 carboxamide MEA, Alcohol denat., Propylene glycol, Deceth-3, Deceth-5, Ethanolamine, Polyquaternium-34, Sodium diethylaminopropylcocoaaspartamide, Sodium acetate, Fragrance, Sodium metabisufite, Resorcinol, EDTA, Phenyl methylpyrazolone, Erythorbic acid, P-phenylendiamine, 2-methylresorcinol, M-aminophenol.

No Ammonia Crème Developer Ingredients: Water, Hydrogen peroxide, Cetearyl alcohol, Trideceth-2 Carboxamide MEA, Ceteareth-30, Glycerin, Pentasodium pentetate, Sodium stannate, Tetrasodium pyrophosphate.

Actif Moisturizing Conditioner Ingredients: Water, Cetearyl alcohol, Glycerin, Behentrimonium chloride, Euphorbia cerifera (Candelilla) wax, Amodimethicone, Cetyl Esters, Isopropyl alcohol, Fragrance, Methylparaben, Trideceth-12, Chlorhexidine, Dihydrochloride, Cetrimonium chloride.

The Color Gel and Crème Developer were combined in the manner taught by the manufacturer and applied to light brown hair swatches for 30 minutes in accordance with the manuafacturer's instructions. The swatches were then rinsed well with water.

Similarly, Formulas D and E from Example 1 were combined with the 20 volume developer composition of Example 2 in and one to one ratio. The mixtures were applied to light brown hair swatches for five minutes, then rinsed well with water.

The chromaticity of the swatches was measured and compared using the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results are as follows.

|  | L | A | b | ΔL | ΔE |
| --- | --- | --- | --- | --- | --- |
| Untreated light brown hair swatches | 27.52 | 6.39 | 10.15 | — | — |
| Color Spa treated hair swatches (30 minutes) | 29 | 7 | 11.4 | 1.48 | 2.03 |
| Formula D (5 minutes) | 29.77 | 7.28 | 12.42 | 2.26 | 3.32 |
| Formula E (5 minutes) | 27.95 | 6.88 | 10.71 | 0.43 | 0.87 |

The above results illustrate that the compositions of the invention provide improved lightening to hair even when it remained on the hair a much shorter period of time (30 minutes versus 5 minutes). In particular, Formula E exhibited a ΔL of 2.26 compared to a 1.48 ΔL for the Color Spa product. It is noted that lightening is an important component of achieving hair color in a reduced period of time. If the hair cannot be adequately lightened in that short period of time, then the color deposit will not be optimal.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An oxidative dye composition comprising one or more oxidative dyes and about 5 to 35% lecithin in a polar solvent that causes the lecithin to form an association structure and oxidatively color hair in about two to five minutes.

2. The composition of claim 1 wherein the oxidative dye comprises at least one primary intermediate and at least one coupler for the formation of oxidation dyes.

3. The composition of claim 1 wherein the association structure is a liquid crystal.

4. The composition of claim 1 wherein the association structure comprises from about 0.1 to about 95% of the composition.

5. The composition of claim 1 wherein the association structure is a micelle.

6. The composition of claim 1 wherein the association structure is a liposome.

7. The composition of claim 1 wherein the composition comprises one or more lipophilic ingredients.

8. The composition of claim 7 wherein the lipophilic ingredients comprise surfactants.

9. The composition of claim 7 wherein the lipophilic ingredients comprise fatty acids.

10. The composition of claim 7 wherein the lipophilic ingredients comprise fatty alcohols.

11. The composition of claim 1 wherein the composition optionally comprises one or more thickening agents, one or more chelating agents, and one or more conditioners.

12. A method for coloring hair or revitalizing colored hair comprising:
  a. application of the composition of claim 1; and
  b. rinsing the composition in (a) from the hair at a time greater than two minutes and less than five minutes.

13. The method of claim 12 which provides Level 2 hair color.

14. A method for treating First Grays comprising:
  a. application of the composition of claim 1; and
  b. rinsing the composition in (a) from the hair at a time greater than two minutes and less than five minutes.

15. A composition for coloring hair comprising; an oxidative dye composition having about 5% lecithin combined with an aqueous developer composition comprising about 0.020-0.5% disodium EDTA, about 918% hydrogen peroxide (35%), about 0.5% acid, about 2% acrylates C10-C30 alkyl acrylate crosspolymer, about 0.5 to about 0.7% tetrasodium EDTA, about 0.7% triethanolamine, about 0.01% disodium phosphate, and QS water.

* * * * *